United States Patent
Kitao

(10) Patent No.: US 9,633,177 B2
(45) Date of Patent: Apr. 25, 2017

(54) BLOOD COLLECTION TUBE MANAGEMENT SYSTEM

(71) Applicant: HOKUYU MEDICS CO., LTD., Osaka-shi, Osaka (JP)

(72) Inventor: Tetsuyu Kitao, Osaka (JP)

(73) Assignee: Hokuyu Medics Co., Ltd., Osaka (JP)

( * ) Notice: Subject to any disclaimer, the term of this patent is extended or adjusted under 35 U.S.C. 154(b) by 0 days.

(21) Appl. No.: 14/688,433

(22) Filed: Apr. 16, 2015

(65) Prior Publication Data
US 2015/0371008 A1 Dec. 24, 2015

Related U.S. Application Data

(63) Continuation-in-part of application No. PCT/JP2014/066234, filed on Jun. 19, 2014.

(51) Int. Cl.
*G06K 7/00* (2006.01)
*G06F 19/00* (2011.01)

(52) U.S. Cl.
CPC .......... *G06F 19/366* (2013.01); *G06F 19/322* (2013.01); *G06F 19/3406* (2013.01)

(58) Field of Classification Search
USPC .......................... 235/486, 487, 385; 436/174
See application file for complete search history.

(56) References Cited

U.S. PATENT DOCUMENTS

| 4,122,947 A | 10/1978 | Falla | |
|---|---|---|---|
| 2007/0036686 A1* | 2/2007 | Hatamian | B01L 3/5021 422/400 |
| 2012/0118954 A1* | 5/2012 | Hagen | G01N 35/00732 235/385 |

FOREIGN PATENT DOCUMENTS

| JP | 63-296733 | 12/1988 |
|---|---|---|
| JP | 7-43365 | 2/1995 |
| JP | 9-34361 | 2/1997 |
| JP | 2001-37743 | 2/2001 |
| JP | 3226750 | 8/2001 |
| JP | 2006-011918 | 1/2006 |
| WO | WO-02/056121 | 7/2002 |

OTHER PUBLICATIONS

"Evacuated single-use containers for venous blood specimen collection", Japanse Industrial Standard JIS T 3233:2011.

* cited by examiner

*Primary Examiner* — Ahshik Kim
(74) *Attorney, Agent, or Firm* — Norris McLaughlin & Marcus, P.A.

(57) ABSTRACT

At the time of blood sampling, blood collection tube information of a blood collection tube concerned is read by blood-collection-tube information reading means, and blood collection subject information 20 on an identification belt as an information recording medium carried by the blood collection subject is read by information-recording-medium reading means. The respectively-read blood collection tube information of the blood collection tube concerned and blood collection subject information of the blood collection subject concerned are correlated with each other and stored in a storage unit by information management means.

8 Claims, 10 Drawing Sheets

F I G. 4
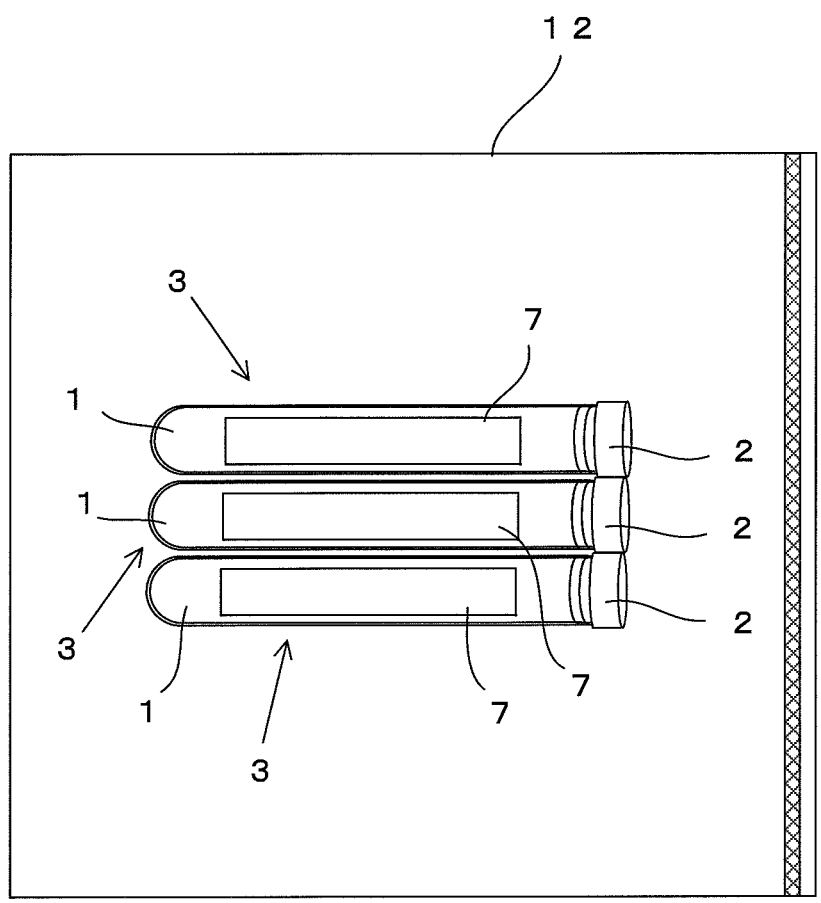

BLOOD COLLECTION TUBE MANAGEMENT SYSTEM

REFERENCE TO RELATED APPLICATION

This is a continuation-in-part of PCT/JP2014/066234 filed Jun. 19, 2014.

BACKGROUND OF THE INVENTION

The present invention relates to a blood collection tube management system which is equipped with a storage unit for storing a variety of data items and manages blood collection tubes for use in a vacuum blood collection method by determining which blood collection tube was used for which blood collection subject.

In hospitals and other medical institutions, the following practice is performed. When a predetermined blood test is performed based on a symptom complaint by a patient (blood collection subject), blood sample is collected from the patient into a blood collection tube by the vacuum blood collection method in a blood collection room of the hospital, for example. The blood sample is sent to a clinical laboratory in the hospital or to a laboratory center outside the hospital where the blood sample is subjected to the predetermined blood test, the results of which are reported.

At this time, the patient, the blood collection tube and the examination items must be reliably correlated. If any one of these items should be erroneously correlated, the patient needs to have his/her blood sampled over again and is subjected to increased burden. In the worst case, the patient may be wrongly diagnosed.

In this connection, there have been proposed systems which are adapted to obviate an error in correlating the patient, the blood collection tube and the examination items. (See, for example, Japanese Patent Publication No. 3226750, paragraphs 0030 to 0033 and Japanese Unexamined Patent Publication No. H9(1997)-34361, paragraphs 0016 and 0020.) JP 3226750 discloses a system where one of the two labels including a barcode and previously affixed to a blood collection tube is separated therefrom and is affixed on a predetermined column of a test card carrying the examination items, the name of a test subject and the like so that the correspondence between the blood collection tube and the test card is determined by reading the barcodes on these labels. Further, JP H9(1997)-34361 discloses a blood collection tube to which a label with a barcode encoding at least a container type, a management number and the like and formed of a transparent material is affixed. This document suggests that correlation between this blood collection tube and a test request form indicating the examination items can be established by assigning a barcode to both the blood collection tube and the test request form.

SUMMARY OF THE INVENTION

The labels affixed to the blood collection tubes in the systems set forth in the above patent documents are normally dispensed by a label dispenser called a labeler installed in the blood collection room. A plurality of barcode labels are dispensed and affixed to a required number of blood collection tubes and a test card or a test request form. After the blood sampling, the barcodes of the labels on the blood collection tubes and the test card are read by a barcode reader so that the blood collection tubes are correlated with the test card or test request form. The blood collection tubes are managed by determining which blood collection tube contains blood collected from which test subject (patient), which examination item is performed on the blood, and the like.

To affix the label, an adhesive surface of a base layer of the label is exposed by peeling off a release sheet of the label dispensed from the labeler, and the exposed adhesive surface is affixed onto the blood collection tube, the test card or the test request form. Such a label affixing operation need be performed at a blood collection site. The release sheet may sometimes be hard to separate, taking much time in the sheet separating operation. Even though the release sheet can be separated, parts of the exposed adhesive surface may be stuck together before the adhesive surface is affixed onto a required place. This leads to the need for the labeler to re-dispense a label with the same barcode. At a stage prior to a practical blood sampling work, a substantial time is taken for an extra work of labeling, resulting in decreased efficiency of the blood sampling work.

It is also desired that the blood sampling is not limited in the blood collection room but the blood samples are also collected from hospitalized patients in an in-patient ward so as to relieve the patients from going to the blood collection room. In this case, as well, the fact remains that a nurse as a sample taker, for example, takes the steps of: picking up blood collection tubes for an inpatient (blood collection subject) as a subject from a predetermined storage space for blood collection tubes at a nurse station or the like; obtaining a required number of labels, each carrying a predetermined barcode, from a labeler disposed at the predetermined storage space for blood collection tubes and affixing the labels to the blood collection tubes, respectively; and bringing the labeled blood collection tubes to the inpatient and collecting blood samples from the inpatient. After all, the blood sampling work still suffers low efficiency. Furthermore, in a case where blood samples are collected from plural inpatients at a time, the nurse must prepare blood collection tubes for each of the inpatients and affix the labels to the blood collection tubes for the individual inpatients. This also leads to fear of misidentification of inpatients where the blood collection tubes prepared for Patient X are mistakenly used for Patient Y, for example.

In recent years, on the other hand, hospitals and the like tend to adopt blood test kits. For example, three major blood tests including a biochemical test for examining hepatic function, kidney function and the like; a blood test for examining red blood cells, white blood cells and blood platelets; and a blood glucose test for examining blood glucose level are commonly packaged. It has become a common practice to previously prepare blood collection tubes for respective uses of the biochemical test, the blood test, and the blood glucose test and to collect blood samples in the individual blood collection tubes for use in the individual tests so that one blood collection step provides for the biochemical test, the blood test and the blood glucose test.

However, even in the case where the three types of tests including the biochemical test, the blood test and the blood glucose test are performed, for example, the status quo is that the sample taker picks up the blood collection tubes for biochemical test, blood test and blood glucose test from the storage space and collects the blood samples in the individual blood collection tubes. The correlation between the blood collection tubes and the blood collection subject is managed only by affixing the above-described labels to the blood collection tubes and reading the barcodes on the labels. The efficiency of the blood sampling work has not been improved yet.

In view of the above problems, the present invention has been accomplished and has an object to improve the work efficiency by alleviating the burden on the sample taker responsible for the blood sampling work and to obviate the error such as the misidentification of patients.

According to the invention for achieving the above object, a blood collection tube management system provided with a storage unit for storing a variety of data items and managing blood collection tubes for use in a vacuum blood collection method by determining which blood collection tube was used for which blood collection subject, includes: a blood-collection-tube information recording part which is formed on a surface of each of the plural blood collection tubes at the time of production of the blood collection tube concerned, and on which blood collection tube information specific to each of the blood collection tubes and including at least information items indicating: the type of test reagent such as separating medium, anticoagulant and blood coagulant corresponding to an examination item and the presence or absence thereof; and the use of the blood collection tube concerned is readably recorded; portable-type blood-collection-tube information reading means for reading the blood collection tube information of the blood collection tube; an information recording medium recording blood collection subject information about a blood collection subject and carried by the blood collection subject; portable-type information-recording-medium reading means for reading the blood collection subject information of the blood collection subject recorded on the information recording medium; and information management means which, at the time of blood sampling, correlates the blood collection tube information of the blood collection tube concerned read by the blood-collection-tube information reading means with the blood collection subject information of the information recording medium carried by the blood collection subject concerned and read by the information-recording-medium reading means, and readably stores the information items in the storage unit. As is implied by FIG. 8, the "information management means" of the system of the invention may be a microcomputer or personal computer of conventional structure, including a CPU (central processing unit), a memory, an input/output circuit, a timer circuit and the like. In that case, the "storage unit" of the system of the invention may be a HD drive. It is noted here that the portable-type blood-collection-tube information reading means and the portable-type information-recording-medium reading means may include a wearable device having a configuration of a pair of glasses or the like.

It is preferred that at least three types of the blood collection tubes with respective uses "for biochemical test", "for blood test" and "for blood glucose test" recorded thereon as the blood collection tube information are bundled as one set of blood collection tubes.

In this case, it is preferred that each of the blood collection tubes in the one set of blood collection tubes is contained in a package formed of a transparent film material.

Further, it is preferred that expiration information indicating an expiration date of the contained blood collection tubes is shown on the package.

It is also preferred that three types of the blood collection tubes with respective uses "for biochemical test", "for blood test" and "for blood glucose test" recorded thereon as the blood collection tube information are prepared; a plurality of the blood collection tubes for biochemical test is contained in a package formed of a transparent film material; a plurality of the blood collection tubes for blood test is contained in a package formed of the transparent film material; a plurality of the blood collection tubes for blood glucose test is contained in a package formed of the transparent film material; and the package for the biochemical test, the package for the blood test and the package for the blood glucose test are bundled as one set of blood collection tubes.

Further, it is preferred that the blood collection tube includes one printed with a use for either of specialized tests including glucose test and hemoglobin test as the blood collection tube information.

Further, it is preferred that the blood collection tube information is represented by a barcode directly formed on a tube surface while the blood collection subject information is represented by a barcode recorded on the information recording medium.

Further, it is also possible to configure a system wherein the blood-collection-tube information reading means is connected to an in-hospital information system via an in-hospital LAN or the like so that the blood collection tube information may be shared in collaboration with the blood collection subject information supplied from the in-hospital information system.

At the time of blood sampling according to the invention, the blood collection tube information of the blood collection tube concerned is read by the blood-collection-tube information reading means while the blood collection subject information on the information recording medium carried by the blood collection subject concerned is read by the information-recording-medium reading means. The respectively read blood collection tube information of the blood collection tube concerned and blood collection subject information of the blood collection subject concerned are correlated with each other and stored in the storage unit by the information management means. Therefore, the operation of affixing the barcode label to the blood collection tube, as performed in the prior art, is no longer required. At the blood collection site, the sample taker such as a nurse responsible for the blood sampling work need only read the blood collection tube information and the blood collection subject information with the respective reading means before and after the blood sampling work so as to integrally store and manage, in the storage unit, the information indicating which blood collection tube is used for which blood collection subject. This is effective not only in reducing the burden on the sample taker for higher work efficiency but also in obviating errors such as misidentification of blood collection subjects.

If at least three types of the blood collection tubes with respective uses "for biochemical test", "for blood test" and "for blood glucose test" recorded thereon as the blood collection tube information are bundled as one set of blood collection tubes, the blood sampling can be carried out by bringing the set of blood collection tubes to the blood collection site. At this time, what is required is to read the blood collection tube information and the blood collection subject information on the respective blood collection tubes of the blood collection tube set concerned by means of the respective reading means. The used blood collection tube and the blood collection subject can be correlated with each other for integral management. What is more, the burden on the sample taker can be reduced for higher work efficiency. In this case, if each of the blood collection tubes in the blood collection tube set is contained in a package formed of the transparent film material, it becomes much easier to handle the blood collection tube set. Further, if the expiration information indicating the expiration period of the blood collection tubes contained in the blood collection tube set is shown, the management of expiration period of the concerned package of blood collection tube set is facilitated. Hence, wasteful disposal of the blood collection tube set due to expiration can be obviated.

If three types of the blood collection tubes with respective uses "for biochemical test", "for blood test" and "for blood glucose test" recorded thereon as the blood collection tube information are prepared; and a package of the plural blood collection tubes for biochemical test, a package of the plurality blood collection tubes for blood test and a package of the plural blood collection tubes for blood glucose test are bundled as one set of blood collection tubes, the handling of the blood collection tubes is facilitated when blood samples are collected from a plurality of blood collection subjects. It is desirable that all the packages contain the same number of blood collection tubes. However, it is also possible to prepare packages containing different numbers (types) of blood collection tubes, respectively.

A case where a specialized test other than the biochemical test and blood test is required can be easily dealt with by preparing a blood collection tube printed with a use for either of the specialized tests including blood glucose test and hemoglobin test as the blood collection tube information.

If the blood collection tube information is represented by the barcode directly formed on the tube surface while the blood collection subject information is represented by the barcode recorded on the information recording medium, the respective information items can be easily read with the reading means such as a barcode reader.

In this case, it is preferred to form the blood collection tube from polyethylene terephthalate (PET), polyacrylonitrile-based resin, polyethylene or the like; to close an opening of the blood collection tube with a plug body formed of natural rubber, synthetic rubber, flexible thermoplastic resin, flexible thermoplastic elastomer or the like; to print the barcode indicating the blood collection tube information on a transparent film coat formed of polyamide-based resin, vinyl chloride resin or nylon 11 (registered trademark) and having a thickness of 0.001 to 1.0 mm (preferably, 0.01 to 0.02 mm); and to cover the whole body of the blood collection tube with this transparent film coat or to affix an IC tag holding the blood collection tube information to the surface of the blood collection tube, followed by covering the whole body of the blood collection tube with the transparent film coat.

BRIEF DESCRIPTION OF THE DRAWINGS

FIG. 4 is a perspective view showing a package of blood collection tube set according to the one embodiment of the invention;

DETAILED DESCRIPTION OF THE INVENTION

Figure 1:
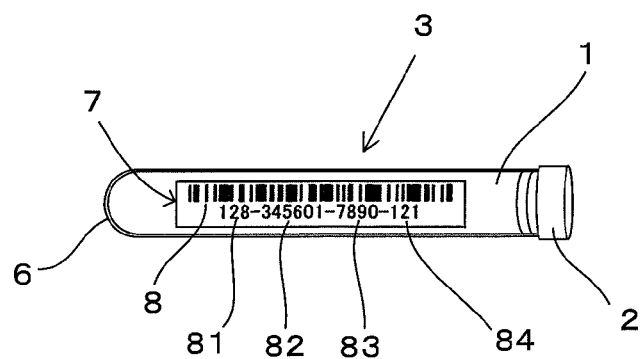
FIG. 1 is a perspective view showing a blood collection tube according to one embodiment of the invention.
Figure 2:
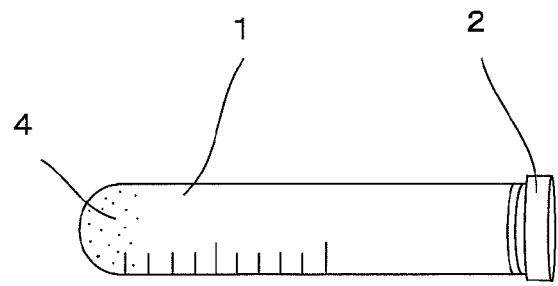
FIG. 2 is a perspective view showing the blood collection tube according to the one embodiment of the invention prior to the formation of a film coat.
Figure 3:
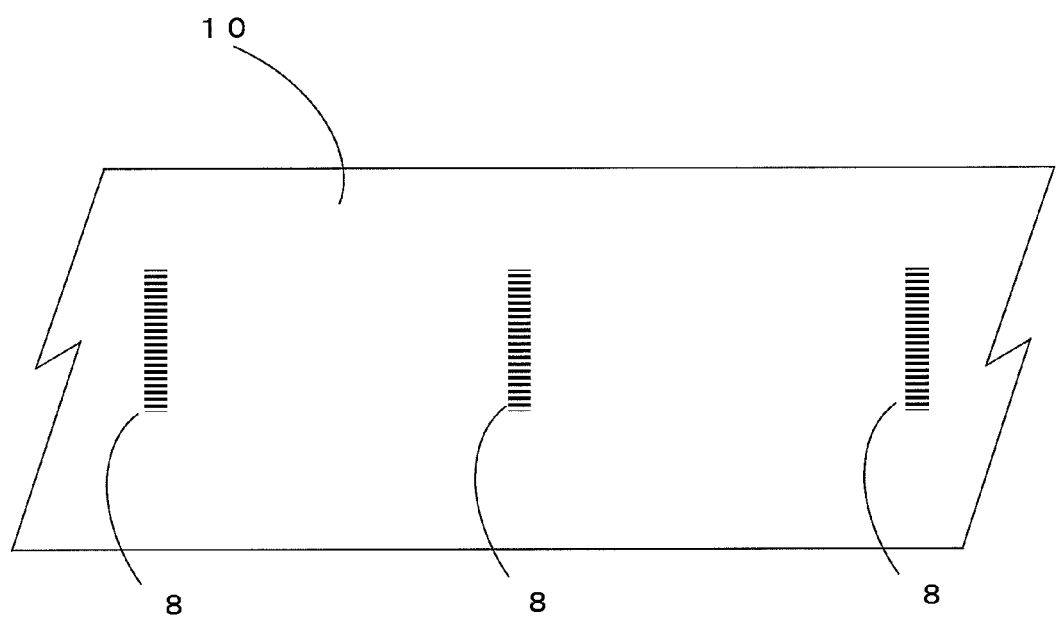
FIG. 3 is a diagram showing a film material printed with barcodes according to the one embodiment of the invention.
Figure 5:
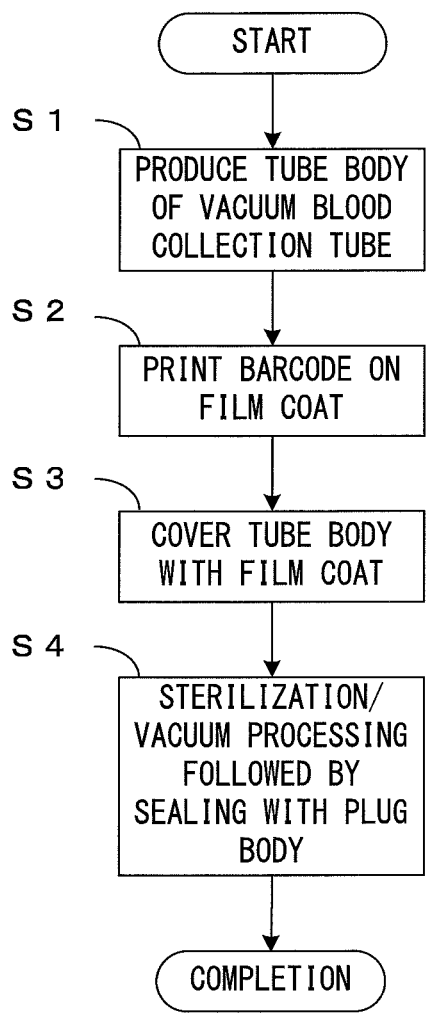
FIG. 5 is a flow chart showing an example of the steps of production procedure of the blood collection tube according to the one embodiment of the invention.
Figure 6:
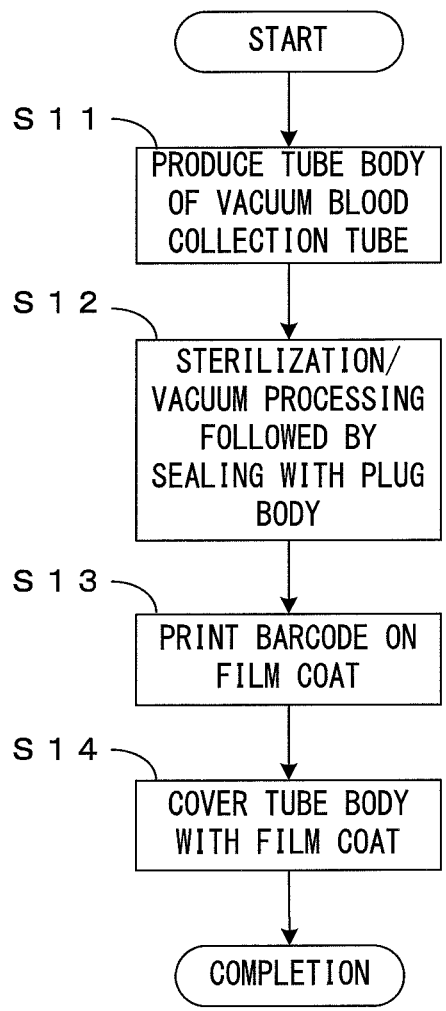
FIG. 6 is a flow chart showing another example of the steps of production procedure of the blood collection tube according to the one embodiment of the invention.

One embodiment of the invention is described with reference to FIG. 1 to FIG. 10B. FIG. 1 is a perspective view of a completed blood collection tube. FIG. 2 is a perspective view of a blood collection tube in the course of production thereof. FIG. 3 is a diagram showing a film material used for forming a film coat. FIG. 4 is a perspective view of a package of blood collection tube set containing three types of blood collection tubes. FIG. 5 and FIG. 6 are flow charts each showing different steps of producing the blood collection tube.

A blood collection tube for use in a vacuum blood collection system is configured as shown in FIG. 1. A tube body 1 formed of glass, for example, has a test tube configuration which is open at one end but is closed at the other end thereof. A blood collection tube 3 is produced by closing the open end of the tube body with a plug body 2 fitted therein. The plug body is formed of rubber, for example. As shown in FIG. 2, the tube body 1 previously contains therein a test reagent 4 corresponding to an examination item. A blood collection tube 3 for biochemical test, for example, contains a silica-based mineral such as silica, kaolin or diatomaceous earth as a blood coagulant for promoting coagulation of blood. A blood collection tube 3 for blood test previously contains heparin or aqueous citrate solution as an anticoagulant for inhibiting the coagulation of blood collected for sedimentation test or examination of coagulation function and a separating medium. A blood collection tube 3 for blood glucose test previously contains sodium fluoride (NaF) or the like as an anticoagulant or glycolysis inhibitor.

As will be described in detail hereinlater, the tube body 1, the inside of which is in sterile and vacuum state, is closed with the plug body 2 and has its outside periphery covered with a film coat 6 whereby the degradation of vacuum degrees in the tube body 1 is prevented. Thus, the expiration period of the blood collection tube is extended. The present inventors have confirmed through experiments that by covering the outside periphery of the tube body 1 with the film coat 6, the expiration period of the blood collection tube 3 is increased about three times more than that of a blood collection tube without the film coat 6.

More recently, PET (Polyethylene terephthalate), besides the above-described glass, has been used for the tube body 1 from the standpoint of easy handling and processing as well as low production costs. Further, PE (Polyethylene) and the like are also usable. However, the materials for the tube body are not limited to these PET and PE. The plug body 2 may preferably employ natural rubber, synthetic rubber, flexible thermoplastic resin, flexible thermoplastic elastomer or the like such as to allow a tip of a blood collection needle to penetrate therethrough easily. The plug body 2 may also be a rubber inside plug of a screw cap.

The film coat 6 may preferably employ a polyamide-based resin, vinyl chloride resin or the like. Nylon 11 (Nylon is a registered trademark of Du Pont de Nemours and Company) having FDA approval is most preferred from the viewpoint of durability and safety. The use of such a translucent material as the material for the film coat 6 permits confirmation of contents in the tube and ensures a higher degree of safety. The film coat 6 may preferably have a thickness of 0.001 to 1.0 mm. Particularly, the most preferred thickness of the film coat is in the range of 0.01 to 0.02 mm. The film coat having such a thickness is easy to handle and maintains translucency.

A blood-collection-tube information recording part 7 is formed on an inside surface of the film coat 6 wound about the tube body 1. Blood collection tube information 8 specific to each blood collection tube 3 and at least including: expiration information indicating an expiration period of a blood collection tube 3 concerned; reagent information indicating the type of test reagent 4 and the presence or absence thereof; and use information indicating which of the biochemical test, the blood test and the blood glucose test the blood collection tube concerned is used for is readably recorded on the blood-collection-tube information recording part 7. When the outside periphery of the tube body 1 is covered with the film coat 6, the blood-collection-tube information recording part 7 is present between the tube body 1 and the film coat 6 so that the information recorded on the blood-collection-tube information recording part 7 during the production of the blood collection tube 3 is readable from outside.

In a case where the film coat 6 is formed by a shrink process, for example, barcodes indicating the blood collection tube information 8 are previously printed and formed, at an interval corresponding to each tube body 1, on an inside surface of a long film material 10, which is wound in a roll, as shown in FIG. 3. The film material 10 is reeled out from the roll and wound about the outside periphery of each tube body 1 in turn, so as to cover the tube body 1 with the film material 10. The film coat 6 is formed on the outside periphery of the tube body 1 by thermally shrinking this film material.

As shown in FIG. 1, the blood collection tube information 8 on the blood-collection-tube information recording part 7 is represented by a barcode conforming to EAN-128 standard, for example. The blood collection tube information 8 includes information specific to each blood collection tube 3, which includes: expiration information 81 indicating the expiration period of the blood collection tube; use information 82 indicating which test the blood collection tube is used for; reagent information 83 indicating the type of test reagent 4, such as separating medium, anticoagulant, or blood coagulant corresponding to the examination item, and the presence or absence thereof; serial number information 84 of each blood collection tube; and the like.

Alternatively, the blood-collection-tube information recording part 7 represented by the barcode conforming to EAN-128 standard may also be directly printed on the outside periphery of the tube body 1. On the tube body 1 with the barcode printed on the outside periphery thereof, the film coat 6 may be formed by the shrink process, a fluidized bed coating process or an electrostatic spray painting process.

As described above, the shrink process is a method where a workpiece (tube body) is covered with a dedicated film, which is thermally shrunk to form a film coat on the outside periphery of the workpiece (the tube body). The fluidized bed coating process is a method where resin powder is fluidized in a resin powder tank by feeding compressed air into the tank from below and a heat treated workpiece (tube body) is dipped in the fluidized powder for a given period of time so that the film coat is formed by allowing the heat of the workpiece (tube body) to fuse the resin powder onto the outside periphery of the workpiece (tube body). The electrostatic spray painting process is a method where an electrostatic field is generated by applying a high DC voltage between the workpiece (tube body) as a positive electrode and a paint spraying device as a negative electrode, and sprayed paint is negatively charged and applied onto an outside periphery of the workpiece (tube body) to form the film coat thereon.

As shown in FIG. 4, three types of blood collection tubes 3 with "for biochemical test", "for blood test" and "for blood glucose test" recorded thereon as the blood collection tube information 8, respectively, are bundled as one set of blood collection tubes, which is put into a package 12 formed of a transparent aluminum, for example. The package 12 is vacuum-sealed by shrink process. The resultant package 12 is stored in a predetermined storage space for blood collection tubes. At this time, the expiration periods of the respective blood collection tubes 3 are indicated on a surface of the package 12.

Next, description is made on a method of forming the film coat 6. There are two methods of forming the film coat 6, as shown in FIG. 5 and FIG. 6. Firstly, description is made on a first method. In a case where glass is used for the tube body 1, for example, the tube bodies 1 are mass-produced by a common glass working method, as shown in FIG. 5 (Step S1). On the other hand, barcodes 9 are previously printed on the film material 10 for forming the film coats 6, as shown in FIG. 3, so as to form the blood-collection-tube information recording parts 7 each including the blood collection tube information 8 varying from one blood collection tube 3 to another (Step S2). Subsequently, the film material 10 printed and formed with the blood-collection-tube information recording part 7 is wound about the tube body 1. The film coat 6 is formed (applied) by the shrink process, for example, so that the outside periphery of the tube body 1 is covered with the film coat 6 (Step S3). Subsequently, the inside of the tube body 1 is sterilized and vacuum-processed. Thereafter, the opening of the tube body 1 is closed and sealed with the plug body 2 (Step S4). In this case, the tube body 1 is sealed with the plug body 2 after the outside periphery of the tube body 1 is covered with the film coat 6. Therefore, the film coat 6 cannot cover so far as a boundary between the tube body 1 and the plug body 2.

Next, description is made on a second method which may proceed as follows. As shown in FIG. 6, the tube bodies 1 are mass-produced by the common glass working method (Step S11). The inside of the tube body 1 is sterilized and vacuum-processed and the opening of the cube body 1 is closed and sealed with the plug body 2 (Step S12). The barcodes 9 are printed on the film material 10 for forming the film coats 6, as shown in FIG. 3, so as to form the blood-collection-tube information recording parts 7 each including the blood collection tube information 8 varying from one blood collection tube 3 to another (Step S13). The film material 10 printed with the blood-collection-tube information recording part 7 is wound about the tube body 1. The film coat 6 is formed (applied) by the shrink process so that the outside periphery of the tube body 1 is covered with the film coat 6 (Step S14). In a case where the inside of the tube body 1 is placed in sterile and vacuum state and the plug body 2 is fitted in the tube body before forming the film coat 6 by thermal shrinkage in the shrink process, as shown in FIG. 6, it is preferred for the film coat 6 to cover the tube body as far as the boundary between the tube body 1 and the plug body 2. By doing so, the boundary between the tube body 1 and the plug body 2 can be hermetically sealed with the film coat 6. Hence, a blood collection tube 3 less susceptible to vacuum degradation can be provided.

Next, description is made on the structure of a blood collection tube management system for providing an integral management of the blood collection tube information 8 and the blood collection subject information when the blood sampling is performed using the blood collection tube 3 having the above-described configuration.

Figure 7:
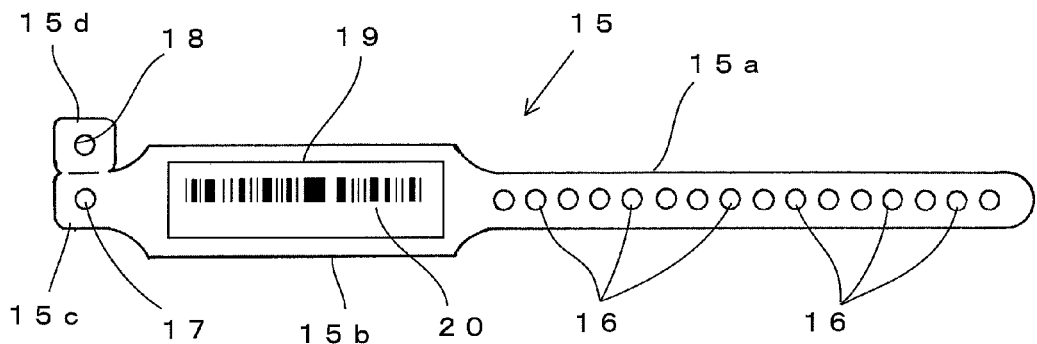
FIG. 7 is a plan view showing an identification band (information recording medium) carried by an inpatient as a blood collection subject in the one embodiment of the invention.

FIG. 7 is a plan view showing an identification band 15 as an example of an information recording medium carried by a blood collection subject or particularly an inpatient. The identification band 15 is generally worn as wrapped around a wrist of the inpatient as an identification bracelet (blood collection subject) This identification band 15 includes: a strip-shaped band body 15a formed with a plurality of punched holes 16; an information displaying part 15b, one end of which is formed integrally with this band body 15a and which displays predetermined blood collection subject information about the inpatient (blood collection subject) and has a greater width than the band body 15a; a fastening part 15c which is formed integrally with the other end of the information displaying part 15b and is penetratedly formed with a fastening hole 17; and a fixing turnover portion 15d formed with a fastening hole 18 overlapped on the fastening hole 17. One of the punched holes 16 that is located at a position corresponding to a size of the wrist of the inpatient is selected. The band 15 is wound about the wrist of the inpatient in a manner that the band body 15a is clamped between the fastening part 15c and the fixing turnover portion 15d at the position of the selected punched hole. The band 15 is worn on the wrist of the inpatient by fixing a hook-like fastener in the three overlapped holes 16, 17, 18.

On this information displaying part 15b, blood collection subject information 20 including the attribute, sex, name, blood type, ID number and the like of the inpatient is directly printed and recorded as a barcode on a predetermined barcode displaying part 19. It is noted that the barcode displaying part 19 may be a patch member such as a labeled tape with the barcode printed thereon, which is affixed to the information displaying part 15b. The information displaying part may be anything that is readable by Information-recording-medium reading means, which is a portable device such as a barcode reader.

Figure 8:
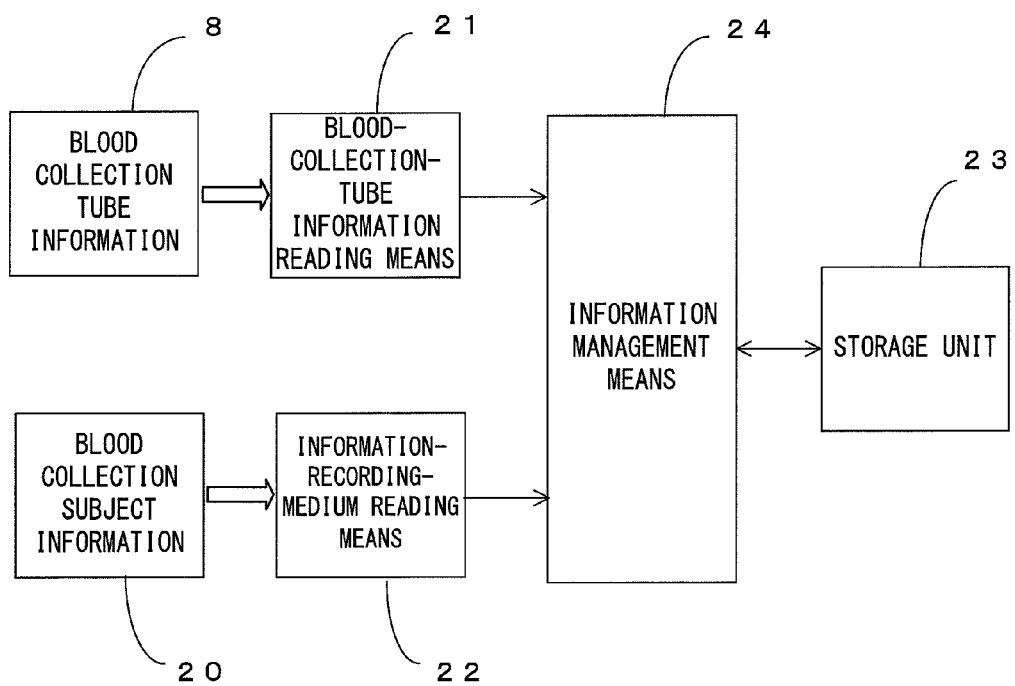
FIG. 8 is a block diagram showing a blood collection tube management system according to the one embodiment of the invention.

FIG. 8 is a block diagram showing the blood collection tube management system. The system includes: portable-type blood-collection-tube information reading means 21 for reading the blood collection tube information 8 of the blood collection tube 3; portable-type information-recording-medium reading means 22 for reading the blood collection subject information 20 recorded as the barcode of the inpatient (blood collection subject) on the barcode displaying part 19 of the identification band 15 as the information recording medium; and information management means 24 which is a microcomputer or personal computer of conventional structure, including a CPU (central processing unit), a memory, an input/output circuit, a timer circuit and the like at the time of blood sampling, correlates the blood collection tube information 8 of the blood collection tube concerned read by the blood-collection-tube information reading means 21 with the blood collection subject information 20 recorded on the barcode displaying part 19 of the identification band 15 of the patient concerned (blood collection subject) and read by the information-recording-medium reading means 22, and readably stores the information items in the storage unit 23 consisting of an HD drive and the like.

Figure 9:
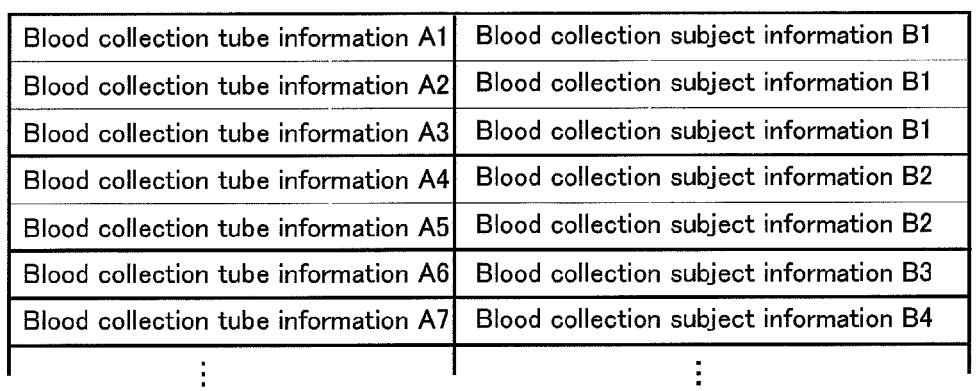
FIG. 9 is a chart showing an example of contents of information stored in a storage unit of the system shown in FIG. 8.

FIG. 9 is a chart showing an example of contents of the information stored in the storage unit 23. Now, description is made on a case where three types of blood collection tubes 3 contained in the package 12 are used for an inpatient B1. A nurse as a sample taker takes out one package 12 containing the three types of blood collection tubes 3 from the storage space for blood collection tubes. At a blood collection site, the package 12 is opened and blood collection tube information A1 (blood collection tube information 8) of a first blood collection tube 3 for biochemical test, for example, is read by the blood-collection-tube information reading means 21. Subsequently, blood collection subject information B1 (blood collection subject information 20) on a barcode displaying part 19 of an identification band 15 of an inpatient (blood collection subject) is read by the information-recording-medium reading means 22. Subsequently, a second blood collection tube 3 for blood test, for example, is similarly taken out from the package 12 and blood collection tube information A2 (blood collection tube information 8) is read. Then, the blood collection subject information B1 (blood collection subject information 20) on the barcode displaying part 19 of the identification band 15 of the inpatient (blood collection subject) is read by the information-recording-medium reading means 22. A third blood collection tube 3 for blood glucose test, for example, is taken out from the package 12 and blood collection tube information A3 (blood collection tube information 8) is read. Subsequently, the blood collection subject information 81 (blood collection subject information 20) on the barcode displaying part 19 of the identification belt 15 of the inpatient (blood collection subject) is read by the information-recording-medium reading means 22. Then, as shown in FIG. 9, respective pairs of the blood collection tube information A1 and the blood collection subject information B1, the blood collection tube information A2 and the blood collection subject information B1, and the blood collection tube information A3 and the blood collection subject information B1 are correlated and stored in the storage unit 23 by the information-recording-medium reading means 22. When the information reading operation is finished, blood samples are actually collected by the nurse. Thus, a series of blood sampling work is finished.

In an example where blood collection tubes 3 for two types of tests are used for a different inpatient 32, blood collection tube information A4 (blood collection tube information 8) of a first blood collection tube for biochemical test, for example, is read by the blood-collection-tube information reading means 21. Then, blood collection subject information B2 (blood collection subject information 20) on a barcode displaying part 19 of an identification band 15 of an inpatient (blood collection subject) is read by the information-recording-medium reading means 22. Subsequently, blood collection tube information A5 (blood collection tube information 8) of a second blood collection tube 3 for blood glucose test, for example, is read. Next, the blood collection subject information B2 (blood collection subject information 20) on the barcode displaying part 19 of the identification band 15 of the inpatient (blood collection subject) is read by the information-recording-medium reading means 22. As shown in FIG. 9, respective pairs of the blood collection tube information A4 and the blood collection subject information 32, and the blood collection tube information A5 and the blood collection subject information B2 are correlated and stored in the storage unit 23 by the information management means 24.

In another example, as shown in FIG. 9, blood collection tube information A6 (blood collection tube information 8) and blood collection subject information B3 (blood collection subject information 20) of another inpatient B3 are correlated and stored in the storage unit 23 by the information management means 24. Further, blood collection tube information A7 (blood collection tube information 8) and blood collection subject information B4 (blood collection subject information 20) of still another inpatient B4 are correlated and stored in the storage unit 23 by the information management means 24. Accordingly, the blood collection tube information pieces A1 to A3 are correlated with the inpatient B1 and stored in the storage unit 23, indicating that the three blood collection tubes A1 to A3 were used for the inpatient B1. The blood collection tube information pieces A4, A5 are correlated with the inpatient B2 and stored in the storage unit 23, indicating that the two blood collection tubes A4, A5 were used for the inpatient B2.

A procedure of such a blood sampling work is described with reference to flow charts of FIGS. 10A and 10B.

Figure 10A:
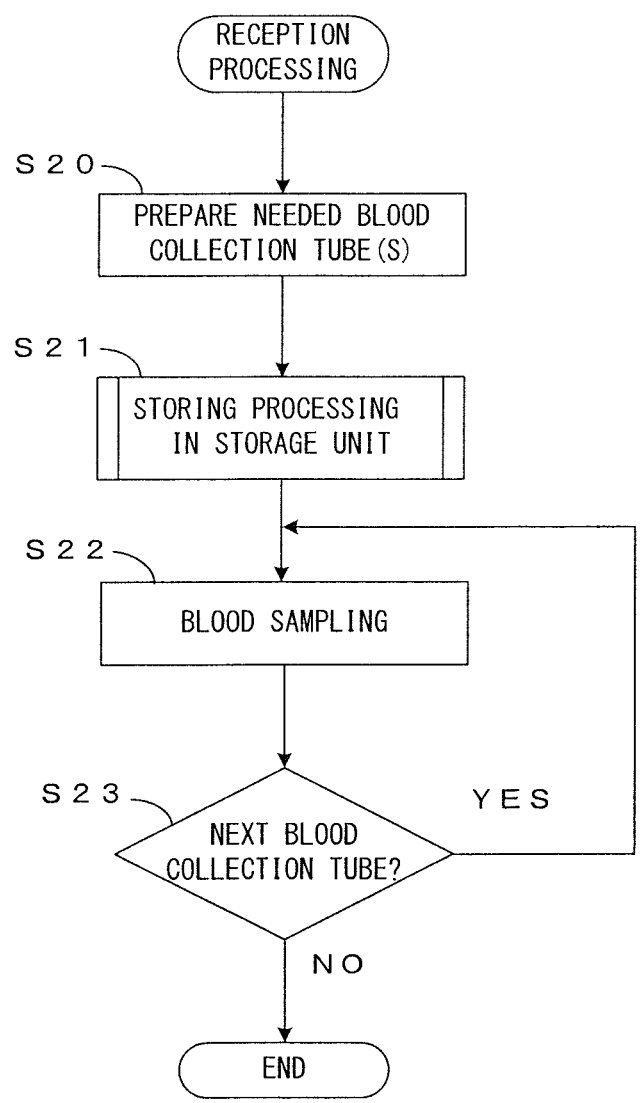
FIGS. 10A and 10B are flow charts illustrating the steps of an operation performed by the system shown in FIG. 8.
Figure 10B:
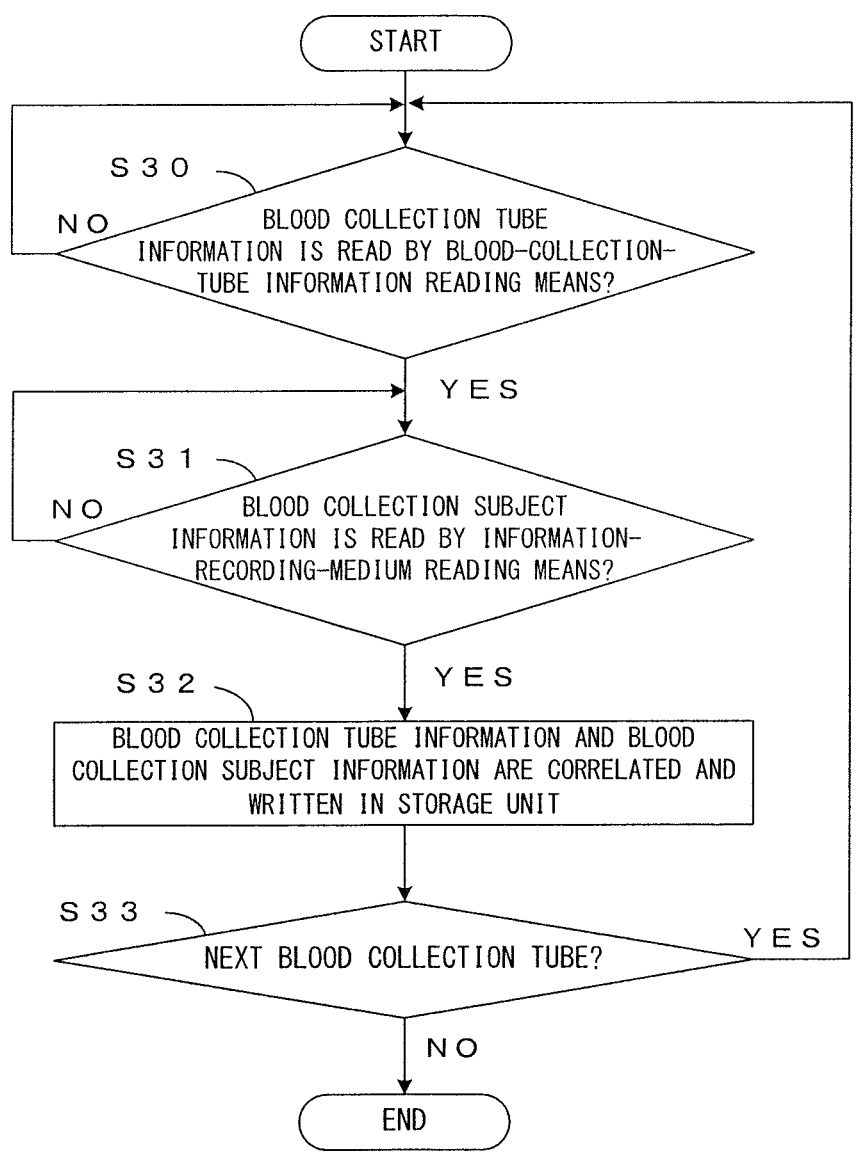

As shown in FIG. 10A, the blood collection tubes 3 needed for the inpatient as the blood collection subject are prepared by the nurse as the sample taker (Step S20). The blood collection tube information 8 of the prepared blood collection tube 3 and the blood collection subject information 20 are correlated and stored in the storage unit 23 by the information management means 24 (Step S21).

This storing processing of the information management means 24 is executed through the following procedure. As shown in FIG. 10B, determination is made as to whether or not the blood collection tube information 8 of the blood collection tube 3 is read by the blood-collection-tube information reading means 21 (Step S30). When the determination result is "NO", the determination of Step S30 is repeatedly executed until the blood collection tube information 8 is obtained and the determination result becomes "YES". When the blood collection tube information 8 is obtained and the determination result becomes "YES", determination is made as to whether or not the blood collection subject information 20 on the barcode displaying part 19 of the identification belt 15 is read by the information-recording-medium reading means 22 (Step S31). When the determination result is "NO", the determination of Step S31 is repeatedly executed until the blood collection subject information 20 is obtained and the determination result becomes "YES". When the blood collection subject information 20 is obtained and the determination result becomes "YES", the correlation between the obtained blood collection tube information 8 and blood collection subject information 20 is established, and the correlated blood collection tube information 8 and blood collection subject information 20 are written in the storage unit 23 (Step S32). Such a processing of Steps S30, S31, and S32 is repeatedly executed until there is not the next blood collection tube 3 and the determination result of Step S33 becomes "NO".

Referring back to FIG. 10A, the flow chart of a blood sampling work, blood sample of the inpatient is collected into the blood collection tube 3 (Step S22). Next, determination is made as to whether or not there is the next blood collection tube 3 for which the blood sampling is not finished (Step S23). If there is the blood collection tube 3 for which the blood sampling is not finished ("YES" in Step S23), the operation returns to Step S22 and blood sample is collected into the blood collection tube 3. If there is not the blood collection tube 3 for which the blood sampling is not finished ("NO" in Step S23), the blood sampling work is finished.

According to the embodiments as described above, when the blood sampling is performed, the blood collection tube information 8 of the blood collection tube concerned is read by the blood-collection-tube information reading means 21 and the blood collection subject information 20 of the identification band 15 as the information recording medium carried by the blood collection subject concerned is read by the information-recording-medium reading means 22. Meanwhile, the read blood collection tube information 8 of the blood collection tube concerned and the read blood collection subject information 20 of the blood collection subject concerned are correlated and stored in the storage unit 23 by the information management means 24. Therefore, the operation of affixing the barcode labels to the blood collection tubes, as practiced in the prior art, is no longer required. Hence, the sample taker such as a nurse responsible for the blood sampling work can integrally store and manage, in the storage unit 23, the information indicating which blood collection tube 3 was used for which blood collection subject simply by reading, at the blood collection site, the blood collection tube information 8 and the blood collection subject information 20 by means of the respective reading means 21, 22 before and after the blood sampling work. This is effective not only in reducing the burden on the sample taker for higher work efficiency but also in obviating errors such as misidentification of blood collection subjects.

In this case, the blood collection tube information 8 is directly formed as the barcode on the inside surface of the film coat 6 or the outside periphery of the tube body 1. Hence, the operation of producing labels printed with the blood collection tube information and affixing the labels by using a labeler, as practiced in the prior art, is no longer required. This leads to the prevention of human errors such as mix-up of labels to be affixed.

The package 12 containing a set of at least three types of blood collection tubes 3 with the respective uses "for biochemical test", "for blood test" and "for blood glucose test" recorded thereon as the blood collection tube information 8 is prepared. This permits the sample taker to perform the blood sampling work by bringing the package 12 of tube set with him/her to the blood collection site. During the work, the sample taker only need to read the blood collection tube information 8 on the individual blood collection tubes 3 contained in the package 12 and the blood collection subject information 20 by means of the respective reading means 21, 22. The blood collection tubes 3 used and the blood collection subject can be correlated with each other and subjected to the integral storage and management. Furthermore, the burden on the sample taker can be reduced for higher work efficiency.

What is more, since a set of blood collection tubes 3 for three types of tests is contained in the package 12 formed of a transparent film material, the packaged set of blood collection tubes 3 is quite easy to handle. Further, the expiration information indicating the expiration period of the blood collection tubes 3 in the package 12 is indicated and hence, the management of the expiration period of the concerned package 12 of blood collection tube set 3 is facilitated. Thus, wasteful disposal of the expired blood collection tube set can be obviated.

A blood collection tube 3 printed with a use for either of the specialized tests including blood glucose test and hemoglobin test as the blood collection tube information 8 may also be prepared to make it easy to deal with a case where a specialized test other than the biochemical test and the blood test is required.

The blood collection tube information 8 is represented by the barcode directly formed on the surface of the tube body 1, while the blood collection subject information 20 is represented by the barcode on the indication band 15 as the information recording medium. Hence, the respective information items can be readily read by using the reading means 21, 22 easy to carry such as a barcode reader. The blood-collection-tube information reading means 21 and information-recording-medium reading means 22 can be implemented in a single barcode reader and hence, cost reduction of the whole system can be achieved.

Since the inside of the tube body 1 is vacuumed after forming the film coat 6 on the outside periphery of the tube body 1, the film coat 6 can be easily formed by a known method. A vacuum blood collection tube having a longer expiration period than that of the prior-art vacuum tubes can be produced. Alternatively, after the inside of the tube body 1 is vacuumed, the film coat 6 is so formed as to cover the outside periphery of the tube body 1 and a part of an outside periphery of the plug body 2. Hence, the blood collection tube 3 less susceptible to vacuum degradation can be provided because the film coat 6 can cover the tube body as far as the boundary between the tube body 1 and the plug body 2.

It is to be noted that the invention is not limited to the above-described embodiments and various changes and modifications may be made thereto without departing from the spirit and scope of the invention.

For example, the above embodiment cites the example where the blood collection tube information 8 is represented by the barcode conforming to EAN-128 standard. However, the blood collection tube information 8 may also be represented by a barcode conforming to another standard or by QR Code (registered trademark).

Figure 11:
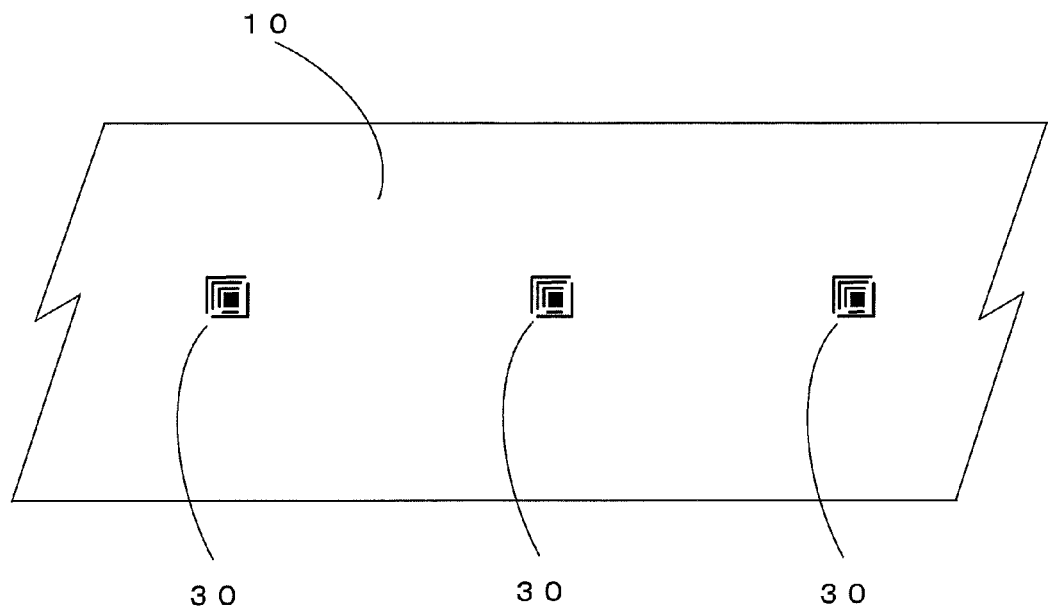
FIG. 11 is a diagram showing a film material with affixed IC tags according to another embodiment of the invention.

As shown in FIG. 11, IC tags 30 containing the blood collection tube information 8 may be previously affixed to the inside surface of the long film material 10 wound in a roll or the IC tags 30 may be previously affixed to the outside periphery of the tube body 1. Subsequently, the film coat 6 may be formed. In this case, the blood-collection-tube information reading means for reading the blood collection tube information 8 contained in the IC tags 30 may be a contact type or a non-contact type.

The above-described embodiment illustrates the examples adopting the fluidized bed coating process, electrostatic spray painting process and shrink process as the method for forming the film coat 6, which is not limited to these. Any practicable processes other than the above are also adoptable.

While the above-described embodiment suggests that the film coat 6 is formed of a polyamide-based resin or vinyl chloride resin, the film coat 6 may also be formed of another translucent material.

While the above-described embodiment illustrates the case where the blood collection subject is the hospital inpatient, the blood collection subject is not limited to the hospital inpatient. The same blood sampling work as that of the above-described embodiment can also be performed on outpatients or medical examinees, providing the same benefits.

Figure 12:
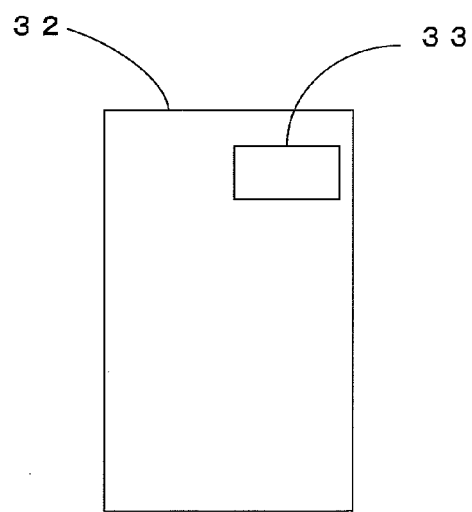
FIG. 12 is a schematic diagram showing an information recording medium used in a blood collection tube management system according to still another embodiment of the invention.

The information recording medium carried by the blood collection subject such as the hospital inpatient is not limited to the above-described identification band 15 but may also be a medical card 32 or patient card made of paper or the like and carried by the patient, as shown in FIG. 12, for example. The blood collection subject information represented by the barcode or the like shown on a blood-collection-subject information displaying part 33 of such a medical card 32 may be read by the information-recording-medium reading means.

The present invention is applicable to the blood sampling work at all kinds of medical settings such as hospitals.

The invention claimed is:

1. A blood collection tube management system comprising:
    (1) a storage unit for storing a variety of data items;
    (2) a plurality of blood collection tubes configured to be used in a vacuum blood collection method, each one of the plurality of blood collection tubes comprising:
        a blood-collection-tube information recording part which is formed on a surface of the blood collection tube at the time of production of the blood collection tube and on which is recorded blood collection tube information specific to the blood collection tube,
        wherein the blood collection tube information comprises information items indicating each test reagent contained in the blood collection tube, and information regarding use of the blood collection tube readably recorded on the blood-collection-tube information part;
    (3) portable blood-collection-tube information reading means for reading the blood collection tube information;
    (4) an information recording medium carried by a person who is a blood collection subject and upon which blood collection subject information about the blood collection subject is readably recorded;
    (5) a portable information-recording-medium reading means for reading the blood collection subject information recorded on the information recording medium; and
    (6) information management means which, at the time of blood sampling, correlates the blood collection tube information read by the blood-collection-tube information reading means with the blood collection subject information read by the information-recording-medium reading means, and readably stores the correlated information items in the storage unit;
    whereby which of the plurality of blood collection tubes was used for which blood collection subject is determined, and
    wherein at least three of the plurality of blood collection tubes having respective uses for biochemical test, blood test and blood glucose test recorded on the respective information recording part thereof as the blood collection tube information are bundled as one set of blood collection tubes.

2. The blood collection tube management system according to claim 1, wherein the one set of blood collection tubes is contained in a package formed of a transparent film material.

3. The blood collection tube management system according to claim 2, wherein expiration information indicating an expiration date of blood collection tubes contained in the package is shown on the package.

4. The blood collection tube management system according to claim 1, wherein
   a plurality of the blood collection tubes for biochemical test are contained in a package formed of a transparent film material, forming a package for biochemical test;
   a plurality of the blood collection tubes for blood test are contained in a package formed of the transparent film material, forming a package for blood test;
   a plurality of the blood collection tubes for blood glucose test are contained in a package formed of the transparent film material, forming a package for blood glucose test; and
   the package for biochemical test, the package for blood test and the package for blood glucose test are bundled as one set of blood collection tubes.

5. The blood collection tube management system according to claim 1, wherein the blood collection tube information recorded on the blood-collection-tube information recording part comprises identification of intended use of the blood collection tube as being for a glucose test or hemoglobin test.

6. The blood collection tube management system according claim 1, wherein the blood collection tube information is represented by a barcode directly formed on the surface of the blood collection tube while the blood collection subject information is represented by a barcode recorded on the information recording medium.

7. The blood collection tube management system according to claim 1, wherein the blood collection tube information further comprises serial number information.

8. The blood collection tube management system according to claim 1, wherein the test reagent contained in the blood collection tube is selected from the group consisting of separating medium, anticoagulant and blood coagulant corresponding to an examination item and presence or absence thereof.

* * * * *